United States Patent [19]

Mazzone et al.

[11] Patent Number: 5,059,904
[45] Date of Patent: Oct. 22, 1991

[54] CONTROL CIRCUIT FOR VARIABLE CHARACTERISTIC ROTATING EDDY CURRENT PROBE

[75] Inventors: Daniel P. Mazzone, Dayton; James D. Hoeffel, Centerville, both of Ohio

[73] Assignee: Systems Research Laboratories, Inc., Dayton, Ohio

[21] Appl. No.: 564,273

[22] Filed: Aug. 8, 1990

[51] Int. Cl.$^5$ .................... G01N 27/72; G01R 33/12
[52] U.S. Cl. .................... 324/226; 324/238; 324/262
[58] Field of Search .............. 324/226, 227, 234, 236, 324/237, 238, 239, 240, 241, 242, 243, 262; 73/618, 619, 620, 621

[56] References Cited

U.S. PATENT DOCUMENTS 4,219,774  8/1980  Rogel et al. .................... 324/262

Primary Examiner—Walter E. Snow
Attorney, Agent, or Firm—Biebel & French

[57] ABSTRACT

A detachable, articulated rotating eddy current inspection tool includes a body member having a connector at one end for mechanically and electrically attaching the body member to a rotating drive member while at the other an eddy current probe is supported for radial movement with respect to the axis of rotation of the body member. A motor located within the body moves a slide on which the probe is mounted while at the same time a counterbalancing slide is moved radially in the opposite direction to maintain said tool in dynamic balance. An encoder housed within said body member senses the location of said eddy current probe with respect to the axis of rotation of said body member. A rotary transformer is used to transfer signals which control the position of the probe and to receive information from the eddy current probe and the encoder. The encoder output signals are modulated by the eddy current probe exciter signal to enable probe position information to be sent through a rotary transformer.

7 Claims, 5 Drawing Sheets

CONTROL CIRCUIT FOR VARIABLE CHARACTERISTIC ROTATING EDDY CURRENT PROBE

BACKGROUND OF THE INVENTION

This invention relates to an improved control circuit for use with a rotating eddy current probe wherein a characteristic of the probe can be varied while it is rotating.

In a retirement-for-cause (RFC) system wherein components, such as aircraft engine parts, are inspected individually for flaws and wear, and accepted or rejected on the basis of that inspection rather than being merely replaced automatically after some predetermined amount of use, regardless of actual condition, uses many different sizes of sensing devices, such as rotating eddy current probes. The two basic types of eddy current probes used are surface probes and hole probes.

A typical RFC inspection system uses many different sizes and configurations of rotating eddy current inspection probes since each surface characteristic requires a probe of the proper configuration because the clearance between the probe's coil and the part surface must be kept to a minimum in order to achieve the necessary sensitivity. For example, a hole inspection probe must be near the same diameter as the hole to be inspected, being only enough smaller to fit into the hole without making any contact with the part.

For each size probe there also must be an accompanying reference standard. Because of the very tight tolerances and difficulty in making the probes and reference standards, this prior art arrangement therefore becomes very expensive.

In addition, each time a different probe is used, there is a substantial amount of time involved in calibrating that probe to the reference standard. Calibration time for each probe is typically about 5 to 7 minutes.

SUMMARY OF THE INVENTION

In the present invention, it has been found advantageous to provide means for varying some characteristic of the eddy current probe, such as its diameter or its angle with respect to the inspected surface in order to reduce the number of probes required for a complete inspection of a component and the time required for performing that inspection.

It is therefore desirable to have a single eddy current hole inspection probe that could conform to a range of diameters and a similar surface probe that can inspect several surface contours. Since there now is only one coil involved for each type of probe, only one reference standard is needed and calibration needs to be performed only once each time the probe is used. It is obvious that such probes would save much time and money. Since a probe would need to be calibrated only once, the inspection time is reduced and the throughout is increased.

By way of example, the high pressure turbine disc in one aircraft engine requires 9 different angle probes. The cost for these probes is about 2,000 each. Each probe must be calibrated and calibration time is about 7 minutes; about an hour total calibration time on each side of the part. A probe that incorporates an angular movement at the coil end could replace these many angled probes. This probe would not reduce the amount of reference standards in this surface probe case, but would however simplify the reference standard design and cost. This probe would also eliminate redundant calibration, thus reducing inspection time and increasing throughput. The calibration time would be reduced from one hour to about 7 minutes per side.

In addition to these benefits of cost and throughput, there is an additional benefit of greater repeatability. Since only one coil is used there is no variation in coil characteristics as is the case with multiple probe use. To the nondestructive evaluation (NDE) scientist, this is an important benefit of this invention.

In the present invention a motor drives a mechanism that controls either the angle of the probe, or its diameter. An encoder indicates the actual position of the probe.

In a rotating eddy current inspection probe, both the probe and probe coils rotate and therefore the rotating probe signal must be coupled to a stationary eddy current instrument in some manner. Also, control of the motor used to vary the diameter or angle of the probe and the encoder that reports actual position must be coupled to the external control circuit.

One common method of coupling the probe signals is by the use of slip rings or brushes. There are high quality slip rings available, but these suffer from some degree of wear and noise. The wear might be tolerable in some situations, but the noise would not be tolerable. This noise could be greatly reduced with the use of a mercury wetted rotary contacts, but for some automated applications however, the eddy current probe must operate in an inverted position, and the mercury wetted contact will not work reliably in an inverted fashion.

In the present invention, an air gap rotary transformer is used to overcome the above mentioned problems, and an eddy current scanning device has been developed and employed using a ganged, eight section rotary transformer. One problem associated with the rotary transformer is losses, and these losses necessitate the use of active eletronics at both sides of the transformer.

It is therefore an object of this invention to provide, in an inspection system of the type that includes a detachable inspection probe, such as an eddy current probe, means for rotating the inspection probe, means for mechanically and electrically attaching the detachable probe to said rotating means, and rotary transformer means for transferring signals to and from the rotating probe, means for changing a mechanical characteristic of the probe while it is rotating, said means including a motor for changing the position of the probe, and an encoder for indicating the position of the probe.

It is a further object of this invention to provide means for controlling the operation of a motor used for changing a characteristic of a probe, including means for supplying electrical power, means for controlling the direction of rotation of the motor, and means for receiving signals from an encoder representing actual motor position through the windings of a rotary transformer.

It is a further object of the invention to provide means for supplying power and direction of rotation information to the motor carried by an eddy current inspection probe through a rotary transformer, said means including a power oscillator and first and second oscillators for selecting the direction of rotation of the motor, the outputs of which are provided to the rotary transformer, means for rectifying and filtering the output winding of the power oscillator winding of the rotary transformer for supplying power to the motor, filter means responsive to a single output winding of the rotary transformer for determining the frequency of the signals, and switch means responsive to the frequency of the signals for controlling the polarity of the voltage applied to the motor and thus the direction of rotation of the motor.

Other objects and advantages of the invention will be apparent from the following description, the accompanying drawings and the appended claims.

DESCRIPTION OF THE PREFERRED EMBODIMENT

Figure 1:
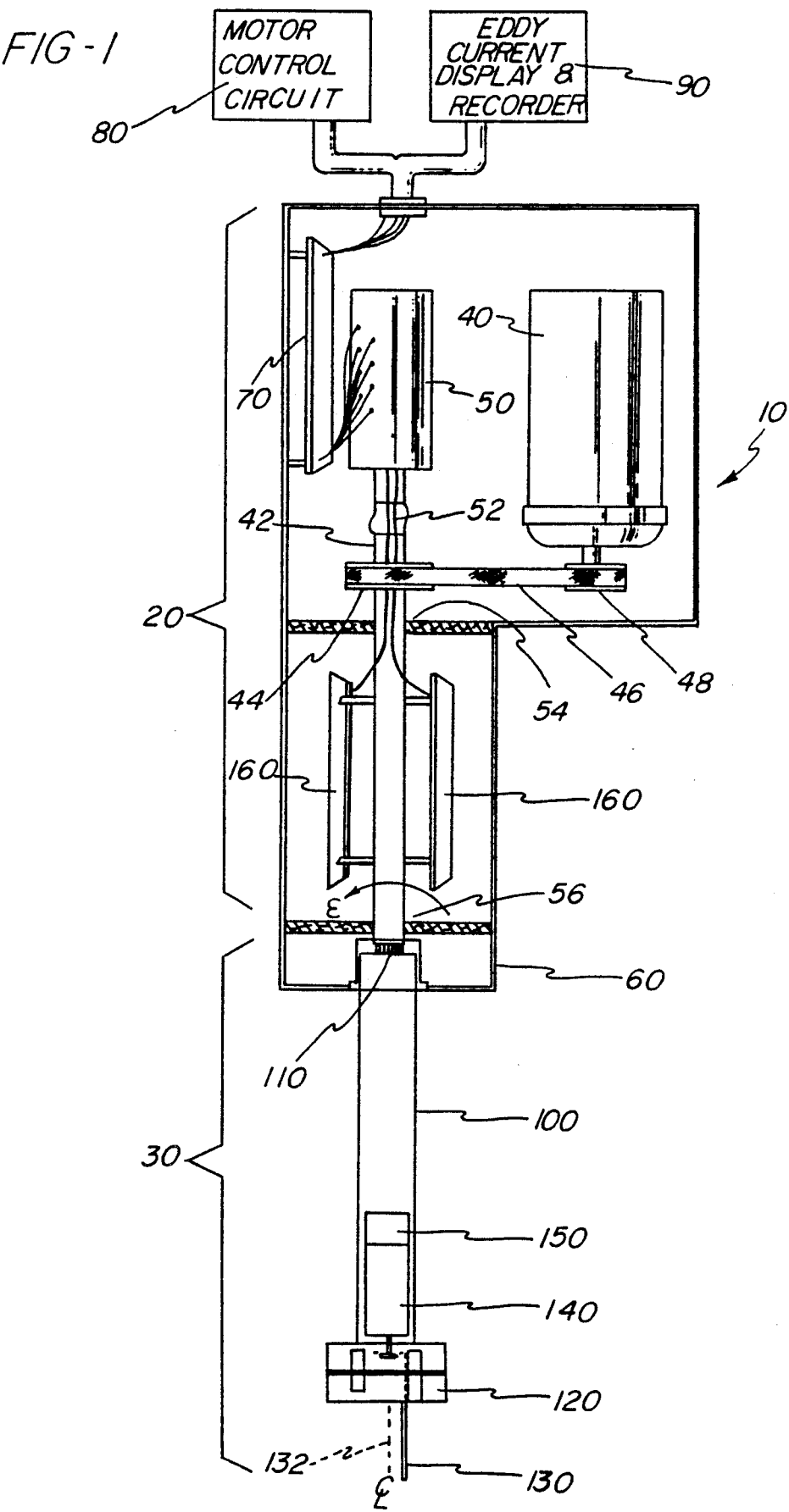
FIG. 1 is a schematic diagram showing generally the components comprising the present invention.

Referring now to the drawing which illustrate a preferred embodiment of the invention, and particularly to FIG. 1, an articulated inspection probe system shown generally at 10 includes a first component or scanner assembly 20 and a second or rotating component or probe 30.

The scanner assembly 20 includes a motor 40 for rotating the probe 30, a rotary transformer 50, a coupling mechanism 60 for detachably connecting the scanner assembly to the probe, a stationary electronics printed circuit board 70 connected to the stationary component of the rotary transformer 50, a motor control circuits 80, and an eddy current display and recording instruments 90.

The scanner assembly 20 is capable of motion in three degrees of freedom in order to position the probe relative to the part or workpiece being inspected. While it is capable of this positioning motion, it is to be understood that many of the components included therein are relatively stationary in the sense that electrical connections to those components of the scanner assembly need only permit a range of movement while the probe 30 is a rotating component and requires a electrical coupling device, such as the rotary transformer 50.

In the preferred embodiment illustrated in FIG. 1, the scanner assembly includes a rotating shaft 42 which is provided with a pulley 44. A drive belt 46 connects the pulley 44 with a pulley 48 at the end of the motor 40. The ratio of the diameters of pulleys 44 to 48 is 2:1, as illustrated. The rotary transformer 50 is mechanically connected to the shaft 42 by a flexible coupling 52. The rotating shaft 42 is supported by bearings 54 and 56.

The probe 30 includes a body member 100 having a at its upper end (as shown in FIG. 1) an electrical connector 110 which mates with a corresponding connector in the coupling mechanism 60. A slot on the side of the body member 100 receives an aligning key in the coupling mechanism for properly positioning the probe to ensure that the electrical connector 110 mates with its counterpart at the end of the shaft 42. Thus, the coupling mechanism 60 provides both mechanical and electrical connections of the probe to the scanner assembly 20.

A mechanically variable mechanism 120 is located at the other end of the body member 100 and this mechanism carries a head member or inspection device, such as an eddy current probe 130. The mechanism 120 is connected to means for modifying a characteristic of the head member and means for sensing the position of said head member. For example, for a hole inspection probe, one characteristic that may be modified is the effective diameter of the probe so that it may be used to inspect holes of different sizes.

The modifying means in the preferred embodiment includes a motor 140 for adjusting the position of the eddy current probe 130 relative to the axis of rotation 132 of the probe 30 while the sensing means includes a position encoder 150 attached to the shaft of the motor 140.

An electrical connection is provided between the eddy current probe 130 and the electrical connector 110. A rotary electronics circuit 160 in the form of a pair of printed circuit boards is mounted for rotation with the shaft 42 within the scanner assembly 20. The rotary electronics circuit 160 receives input signals from the eddy current probe 130 through the connector 110 and its output is connected to the rotating component of the rotary transformer 50 for providing the necessary motor control signals, for sensing the output of the encoder as well as supplying the device current to and the output signal from eddy current probe.

The rotary electronics circuit 160 is compatible with various types of probes, such as the variable diameter probe describe herein as well as a variable angle probe. By associating the rotary electronics circuit with the scanner assembly, only the necessary mechanical structure is contained in the removable probe 30.

Figure 2:
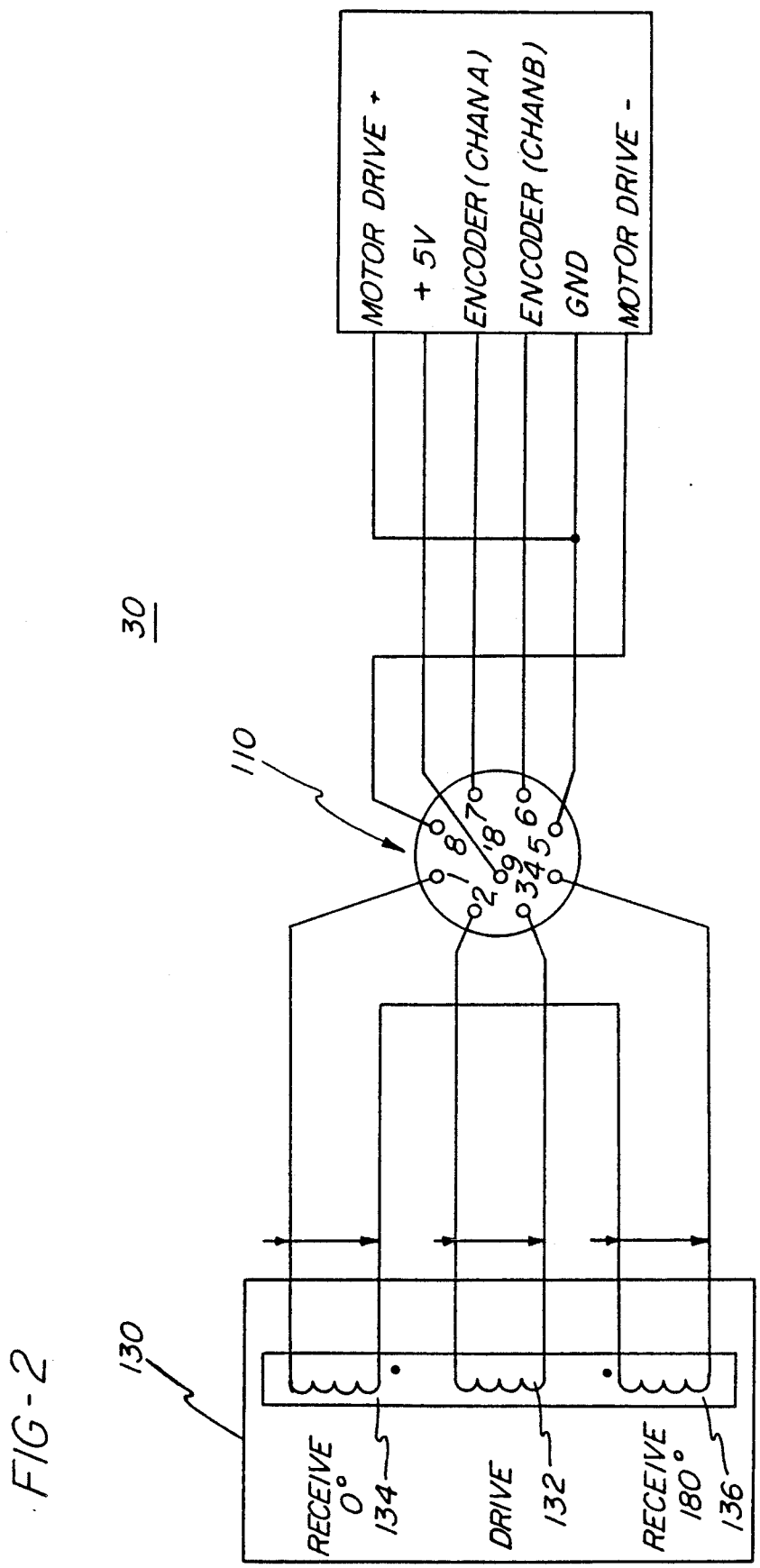
FIG. 2 is an electrical diagram showing the connection between the electronic components within the probe and its electrical output connector.

FIG. 2 is an electrical diagram showing the connection between the electronic components within probe 30 and its eletrical output connector 110. Within the eddy current probe 130 is a set of eddy current coils, including a drive coil 132 and a pair of sensor coils 134 and 136. These coils are connected to pins 1-4 of the probe half of the connector 110. Pins 5-9 are connected to the motor 140 and the encoder 150 as shown.

Figure 3:
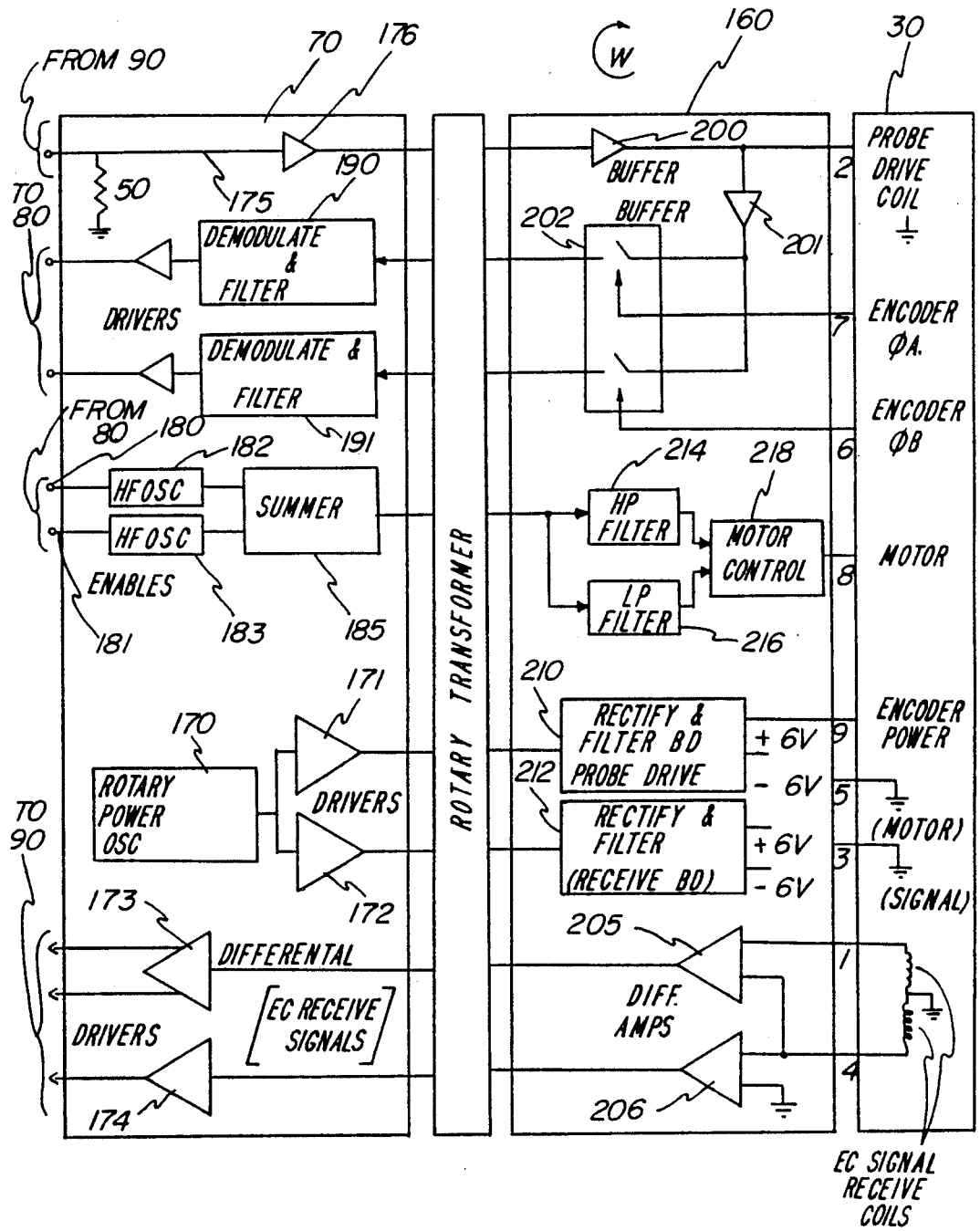
FIG. 3 is an electrical block diagram showing the relationship among the probe components, the rotating electronic circuit components, the rotary transformer, the stationary electronics circuit components, and the control and output circuits.

FIG. 3 is an electrical block diagram of both the stationary electronics circuit 70 and the rotary electronics circuits 160, the rotary transformer 50, and the various components in the probe 30.

The stationary electronics circuit 70 include an oscillator 170 and current drivers 171 and 172 for supplying power to the rotary electronics circuits through the rotary transformer 50. Also included are current drivers 173 and 174 which receive and amplify signals from the eddy current probe and to provide these signals to the eddy current instrument 90. A probe drive signal on line 175 is generated in the eddy current instrument 90, and is applied to the rotary transformer 50 via current driver The micromanipulator motor 140 is controlled by signals on lines 180 and 181 from the motor control 80. These lines are connected to a high frequency oscillator 182 and low frequency oscillator 183, respectively. The oscillator outputs are connected to summer 185 whose output is applied to the rotary transformer 50.

Data from the encoder 150 is received by demodulator and filter circuits 190 and 191 and transferred by drivers back to the motor control 80.

Referring to the rotary electronics circuit 160, it includes a current buffer 200 through which current to drive the probe drive coil 132 is provided. Current from the buffer is also used to supply a modulating signal to a analog switching circuit 202; this circuit receives the output signals from the encoder 150 as will be explained.

A pair of differential amplifiers 205 and 206 receive the output signals from the eddy current coils 134 and 136, respectively. The differential amplifier 205 has a gain of five. The amplifier 206 uses one received signal for an absolute eddy current measurement.

A pair of rectifier and filter circuits 210 and 212 supply DC power to the circuits on the board 160 and to the encoder 150. High pass filter 214 and low pass filter 216 sense the output of the summer 185 and provide control signals to operate the micromanipulator motor 140 either clockwise or counterclockwise, depending upon which oscillator 182, 183 has been activated. Using a dual frequency motor control requires the use of only one section of the rotary transformer 50. In the preferred embodiment, the high frequency signal is 100 kHz while the low frequency signal is 10 kHz. Thus, the operator can select the direction of motor rotation merely by operating a switch in the control circuit 80 to enable one or the other of the oscillators, and the result will be the application of either positive or negative polarity to the motor 140 to control its direction of rotation.

The output from the encoder 150 is a conventional square wave, two line quadature signal. These are direct current signals that are either one direct current polarity or another, consequently they cannot be transferred directly through the rotary transformer to the control circuit 80. In the present invention, an analog switching circuit 202 provides the solution. The encoder output is modulated by a carrier frequency that is derived from the probe drive coil excitation circuit through buffers 200 and 201. The carrier frequency is approximately 1 to 2 MHz, and therefore these signals easily pass through the rotary transformer where they are then demodulated and converted into standard TTL outputs by the demodulator and filter circuits 190 and 191.

Figure 4:
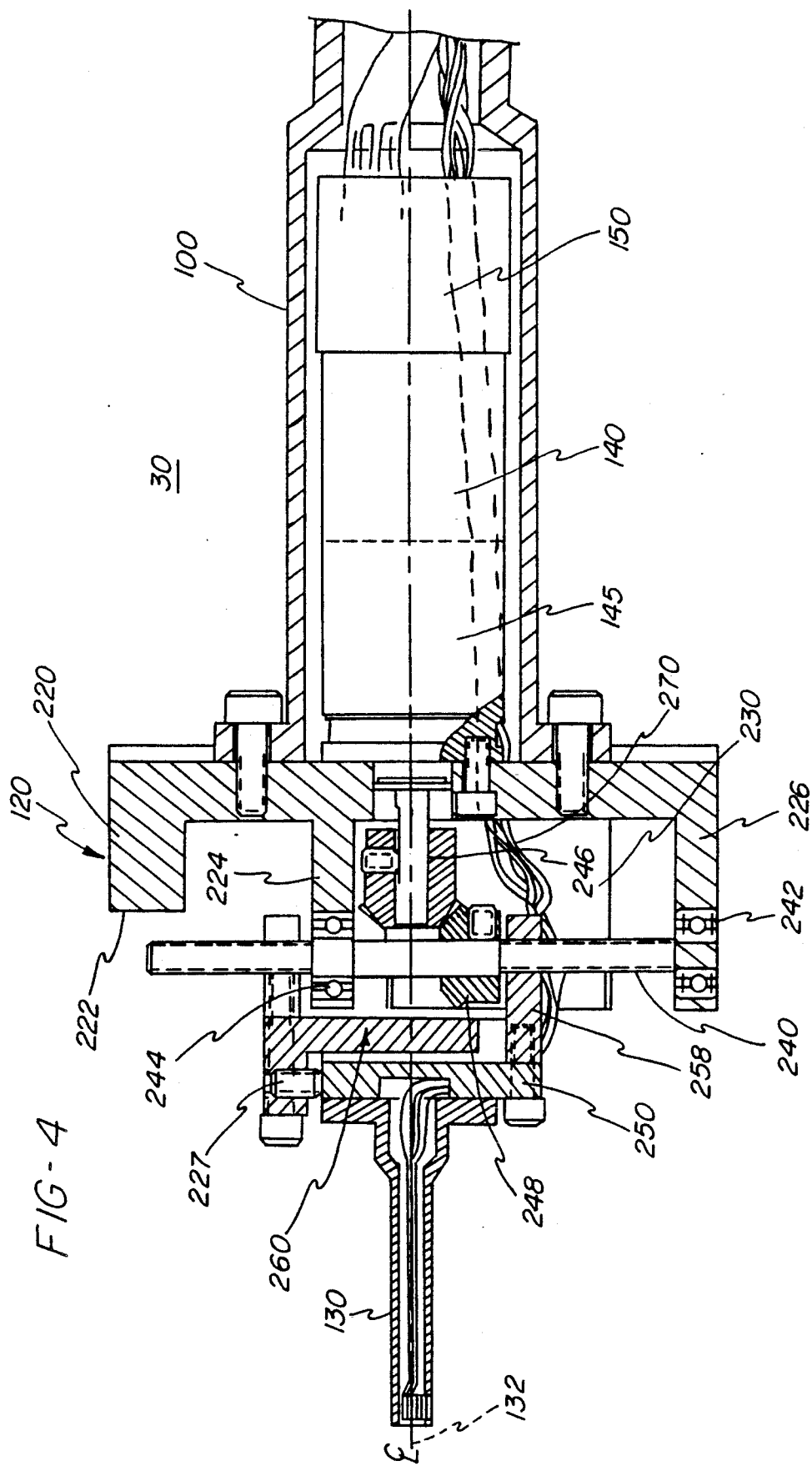
FIG. 4 is an elevational view, partly in cross section, of a variable diameter eddy current probe constructed according to this invention.
Figure 5:
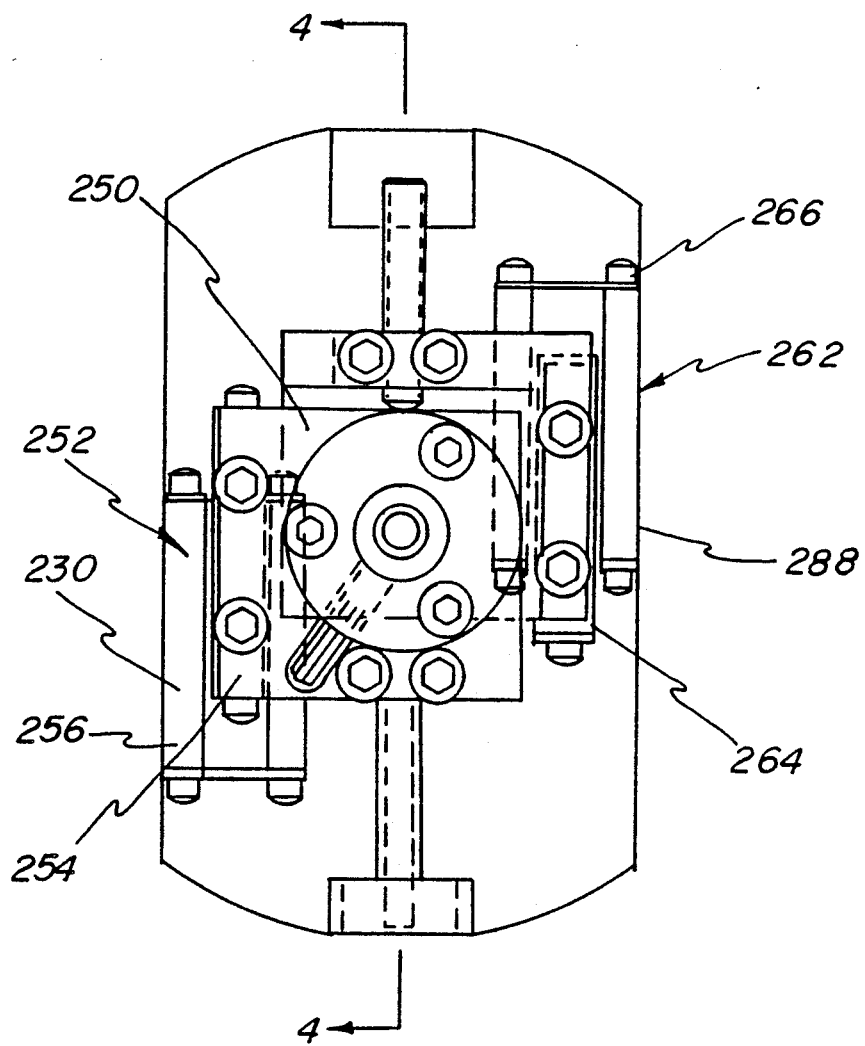
FIG. 5 is an end view of the variable diameter eddy current probe shown in FIG. 4.

A variable diameter probe 30 is shown in FIGS. 4 and 5. This probe has a similar housing 100 as prior art rotating eddy current hole inspection probes, as least in the size and configuration of its upper portion, to allow it to interface to the existing scanner assembly coupling mechanism 60. This permits the automatic exchange of probes, when necessary.

As shown, the housing 100 has a reduced diameter end 104 that is provided with a slot 106 on the side to receive an aligning pin in the coupling mechanism 60. This mechanical arrangement ensures proper orientation of the probe before the electrical connector 110 mates with its counterpart at the end of the shaft 42.

The motor 140 and the encoder 150 contained within the housing 100 are commercially available components. In the preferred embodiment, the motor 140 is a Series 1516 DC micromotor, a gearbox 145 is a Series 15/5 device, and the encoder 150 is a Series HE magnetic encoder, all manufactured by Micro Mo Electronics, Inc. of St. Petersburg, FL.

The mechanically variable mechanism 120 shown in FIGS. 4 and 5 is designed to vary the effective diameter of the eddy current probe so that a single probe can be used to inspect hole of several different diameters. The mechanism 120 includes a frame member 220 having outwardly extending bosses 222, 224, 226, 228 and 230. A differential screw 240, having a pitch of 40 threads per inch, is supported at one end by a bearing 242 in boss 226 and at an intermediate point by a bearing 244 in boss 224. A gear 246 attached to the output shaft of motor gearbox 145 meshes with a gear 248 secured to the screw 240. Thus, the screw 240 will rotate in either the clockwise or counterclockwise direction under the direction of the motor 140.

The eddy current probe 130 is supported on a platform 250, and the platform in turn is slidably mounted on a ball slide mechanism 252, such as a Series C microminiature ball slide manufactured by Deltron Precision, Inc. This mechanism includes a slide 254 onto which the platform 250 is secured, and a base 256 which is bolted onto on the boss 230 extending from the frame 220. The platform 250 carries a threaded member 258 that is associated with the screw 240 so that the eddy current probe 130 may be moved varying distances from the center line 132 under the control of motor 140.

A counterbalancing mechanism is also provided to prevent vibration from occurring as the eddy current probe is moved away from the centerline. This mechanism includes a platform 260 that is supported by a ball slide mechanism 262. This mechanism includes a slide 264 onto which the platform 260 is secured, and a base 266 which is bolted onto on a boss 228 extending from the frame 220. The platform 260 carries a threaded member 268 that is associated with the screw 240 so that the platform 260 will be moved the same distance from the center line 132 in the opposite direction as the platform 250 since the pitch of the threads on this portion of the screw are reversed. Note that the boss 222 merely provides a fixed counterbalance for the boss 226 at the opposite side of the mechanism. Thus, no matter how far the eddy current probe 130 is moved away from the centerline 132, the system will remain in balance, permitting the probe to be rotated by the scanner at high speeds without vibration.

Electrical connection between the coils in the eddy current probe and the connector 110 are provided by wires 270 which are routed through an opening in the platform 250 and into the housing and past the motor and encoder.

In operation, the motor is rotated in one direction until the platforms are mechanically restrained from further motion. Since this is the same location each time, this location provides a starting point, thus allowing the encoder 150 thereafter to indicate accurately the position of the probe 130 relative to the center line 132.

The resolution of the system is a function of the ratio of the gearbox 145, the ratio of the gears 246 and 248, and the pitch of the screw 240. In the present invention, there are 4000 encoder output pulses for each 0.001 inch of lateral travel of the probe 130.

Thus, a single probe can be used to inspect holes of different diameters. It is only necessary to calibrate the probe 130 once against a calibration standard since subsequent changes in the effective diameter of the probe does not affect the electrical characteristics of the eddy current sensing coils.

While the form of apparatus herein described constitutes a preferred embodiment of this invention, it is to be understood that the invention is not limited to this precise form of apparatus and that changes may be made therein without departing from the scope of the invention, which is defined in the appended claims.

What is claimed is:

1. In an inspection system including a detachable inspection probe, means for rotating said inspection probe, means for mechanically and electrically attaching said detachable probe to said rotating means, and means for transferring signals to and from said rotating inspection probe, the improvement comprising means for changing a mechanical characteristic of said inspection probe while it is rotating, said means including a motor carried by said probe for changing the position of said inspection probe, and an encoder for indicating the position of said probe, means for controlling said motor through said signal transferring means, and means for receiving signals from said encoder through said signal transferring means.

2. The inspection system of claim 1 wherein said signal transferring means is a rotary transformer.

3. The inspection system of claim 2 further including means for modulating the output signals from said encoder prior to application of said signals to said rotary transformer, and means for demodulating said modulated encoder signals.

4. The inspection system of claim 2 further including means for controlling the direction of rotation of said motor through a single winding of said rotary transformer, said direction controlling means including first and second oscillators for selecting the direction of rotation of said motor, the output of one of which is provided to a primary winding of said rotary transformer, filter means connected to a corresponding output winding of said rotary transformer for determining the frequency of said selected oscillator to determine the direction of rotation of said motor, and switch means responsive to the frequency of said selected oscillator for controlling the polarity of the voltage applied to said motor and thus its direction of rotation.

5. The inspection system of claim 1 wherein said mechanical characteristic is the effective diameter of said probe, and wherein said diameter is changed by changing the radial location of said eddy current probe with respect to the axis of rotation of said rotating means.

6. The inspection system of claim 1 where in said inspection probe is an eddy current probe.

7. In an eddy current inspection system including a detachable eddy current probe, means for rotating said eddy current probe, means for mechanically and electrically attaching said detachable probe to said rotating means, and rotary transformer means for transferring signals to and from said rotating eddy current probe, the inprovement comprising means for changing a mechanical characteristic of said eddy current probe while it is rotating, said means including a motor carried by said probe for changing the position of the eddy current probe, and an encoder for indicating the position of the eddy current probe, means for supplying electrical power to a primary winding of said rotary transformer, and means for rectifying the output from a corresponding secondary winding of said rotary transformer for supplying power to rotate said motor, means for controlling the direction of rotation of said motor including first and second oscillators, the output of one of which is provided to a single winding said rotary transformer, filter means responsive to a corresponding output winding of said rotary transformer for determining the frequency of the selected oscillator to determine the direction of rotation of said motor, and switch means responsive to the frequency of said selected oscillator for controlling the polarity of the voltage applied to said motor, and means for modulating the output signals from said encoder prior to application of said signals to said rotary transformer, and means for demodulating said modulated encoder signals.

* * * * *